United States Patent [19]

Ophoff et al.

[11] 4,437,005
[45] Mar. 13, 1984

[54] NONDISPERSIVE INFRARED GAS ANALYZER

[75] Inventors: Paul-Arthur Ophoff, Wörth; Johann Weinel, Karlsruhe, both of Fed. Rep. of Germany

[73] Assignee: Siemens Aktiengesellschaft, Berlin & Munich, Fed. Rep. of Germany

[21] Appl. No.: 322,210

[22] Filed: Nov. 17, 1981

[30] Foreign Application Priority Data

Nov. 17, 1980 [DE] Fed. Rep. of Germany ....... 3043332

[51] Int. Cl.³ .............................................. G01J 1/00
[52] U.S. Cl. .................................... 250/343; 250/351
[58] Field of Search ............. 250/338, 343, 351, 354.1

[56] References Cited

U.S. PATENT DOCUMENTS

| 3,105,147 | 9/1963 | Weilbach et al. | 250/43.5 |
| 3,678,269 | 7/1972 | Malek | 250/343 |
| 4,051,371 | 9/1977 | Dewey, Jr. et al. | 250/343 |
| 4,163,899 | 8/1979 | Burough | 250/343 |

*Primary Examiner*—Janice A. Howell

*Attorney, Agent, or Firm*—Kenyon & Kenyon

[57] ABSTRACT

A nondispersive infrared gas analyzer of the type wherein gas-filled chambers are arranged in the path of modulated infrared radiation. A measurement pickup is provided for producing a signal responsive to the response of a gas contained in the chamber to the infrared radiation. The infrared radiation is produced by a source of infrared radiation which is powered by a pulsed energy supply, the pulsed energy supply being responsive to control signals so as to provide pulses which have a duty cycle which is less than 1, and preferably between 0.1 and 0.5. The duration of the pulses is controlled in response to the maximum value of a measuring signal of an output of a measuring pickup. In other embodiments, the duration of the pulses may be determined empirically, by calculation, or by means of peak detector. This arrangement provides almost 100% modulation while considerably reducing power consumption and without loss of sensitivity. As such, the invention is particularly useful in battery-operated nondispersive infrared gas analyzer equipment adapted for field use.

5 Claims, 4 Drawing Figures

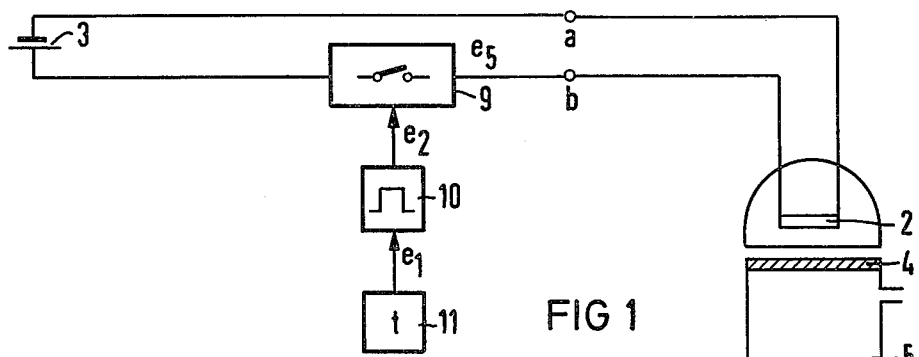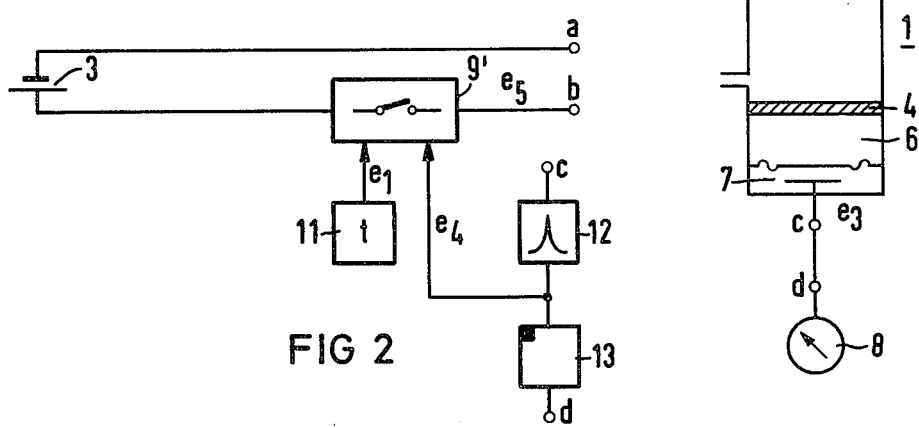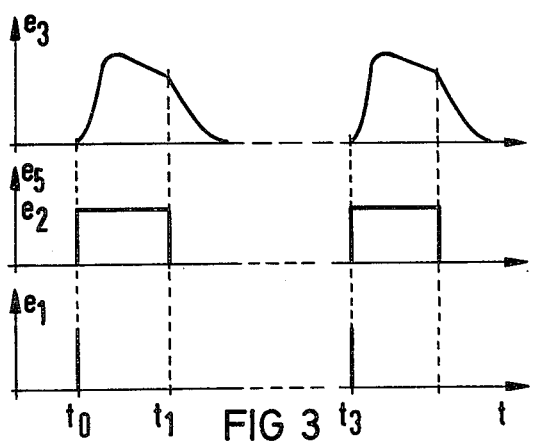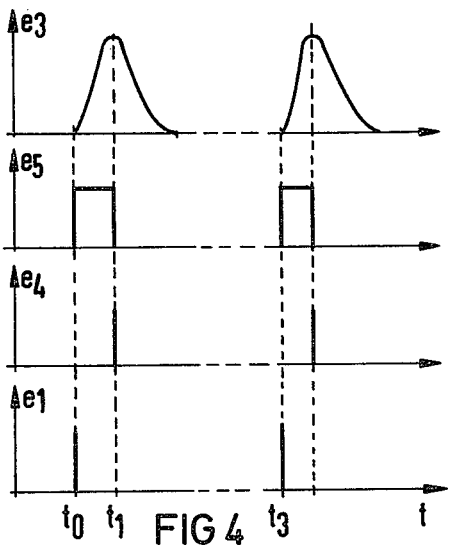

NONDISPERSIVE INFRARED GAS ANALYZER

BACKGROUND OF THE INVENTION

This invention relates to nondispersive infrared gas analyzers, and more particularly, to a nondispersive infrared gas analyzer of the type having a temperature radiator operated by a pulsed energy supply; the analyzer having gas-filled chambers arranged in the path of the modulated infrared radiation and a measuring pickup for producing an electrical measurement signal.

The principles and modes of operation of nondispersive infrared gas analyzers are well known. Modulation of the infrared radiation, which enhances the measurement effect, is frequently achieved by means of an aperture wheel which is rotated by an electric motor and which periodically interrupts the radiation. Although this arrangement achieves a desired 100% modulation, a relatively large amount of continuous energy is required for the temperature radiator to maintain it continuously at the operating temperature. In addition, the electrical motor which operates the aperture wheel also requires substantial continuous energy. Such substantial energy drains are particularly disadvantageous in battery operated equipment which is used in field investigations. In addition, equipment which is used in the field is subjected to mechanical shock and vibration, and must be operated in different positions, thereby adversely affecting the reliability of the mechanically operated parts.

In one known nondispersive infrared gas analyzer which is described in U.S. Pat. No. 3,105,147, some of the above-mentioned disadvantages are overcome by the use of an infrared radiation source which is modulated by a pulsed power supply. However, in order to achieve the desired 100% of modulation, the known pulsed radiators must be operated at very low pulse frequencies, thereby substantially reducing the sensitivity of the measuring device. Such a reduction in sensitivity is particularly acute in equipment which utilizes selective pneumatic receivers.

It is, therefore, an object of this invention to provide an improved nondispersive infrared gas analyzer which is useful as field equipment which operates without the need for a line power supply.

It is a further object of this invention to provide a nondispersive infrared gas analyzer wherein a high degree of modulation is achieved having undiminished sensitivity and low power comsumption.

SUMMARY OF THE INVENTION

The foregoing and other objects are achieved by this invention which provides a nondispersive infrared gas analyzer wherein the duty cycle of the pulsed energy supply is less than unity. In a preferred embodiment, the duty cycle of the pulsed energy supply is between 0.5 and 0.1. The pulse duration is controlled as a function of the maximum value of the measurement signal. The maximum, or peak, value can be determined from the shape of the response curve of the measuring pickup empirically or by calculation. A pulse generator which controls a power switch between the power source and the temperature radiator can then be adjusted accordingly.

The duration of the intervals between pulses is selected so that the temperature radiator has time to cool sufficiently so that it no longer emits radiaton which influences the measuring pickup. Very short pulse durations can be achieved if the temperature radiator is operated at several times its continuous rated power because the peak of the measuring signal is reached more quickly as a result of the increased emission of radiation energy.

The pulse duration is automatically controlled as a function of the maximum value of the measurement signal by means of a bistable power switch located between the power source and the temperature radiator. The power switch is closed by operation of a clock generator which produces pulses which are spaced in time according to the sum of the pulse and interval durations. The opening of the switch is achieved by a maximum-value detector which is operated by the measuring signal at its input.

The power requirements of the nondispersive infrared gas analyzer, which are already reduced by the elimination of the electric motor interrupter wheel drive, can be reduced still further by the pulsed operation, in accordance with the invention, without loss of measuring sensitivity.

BRIEF DESCRIPTION OF THE DRAWINGS

Comprehension of the invention is facilitated by reading the following detailed description in conjunction with the annexed drawings, in which:

FIG. 1 is a schematic representation of an embodiment of the invention;

FIG. 2 is a schematic representation of a further embodiment of the invention;

FIGS. 3 and 4 are timing diagrams useful in explaining the operation of the invention.

DETAILED DESCRIPTION

FIG. 1 shows a schematic representation of a nondispersive infrared gas analyzer 1 having a temperature radiator 2. Temperature radiator 2 may illustratively be formed as a coiled resistance wire which is supplied electrical energy from a power supply 3. The radiation energy which emanates from temperature radiator 2 is focused by known means and is propagated through a measuring chamber 5 which is provided with windows 4. Measuring chamber 5 is filled with a gas mixture (not shown) to be analyzed. A receiving chamber 6 is filled with a particular gas component to be detected. The volume of receiving chamber 6 is increased in response to the thermal energy which is absorbed by the gas component therein which exerts a corresponding pressure on a diaphragm capacitor which is arranged, in this embodiment, as a measuring pickup 7. Measuring pickup 7 delivers an electrical measuring signal $e_3$ which corresponds to the excursion of the movable diaphragm. Electrical measuring signal $e_3$ is conducted to a device 8 which processes and/or indicates the measurement value. Pulsed interruption of the power supply is achieved by a monostable electronic power switch 9 which is arranged in the circuit between temperature radiator 2 and power supply 3. Electronic power switch 9 is controlled by an electrical signal $e_2$ produced at the output of a pulse generator 10. Pulse generator 10 is triggered by clock pulses $e_1$ produced at an output of a clock generator 11.

FIG. 3 is a timing diagram which illustrates the time relationships between signals $e_1$, $e_2$, and $e_3$. The waveforms are shown on parallel time scales t. At a time $t_0$, a clock pulse $e_1$ of clock generator 11 triggers pulse generator 10 which delivers a control pulse lasting until the time $t_1$. This control pulse causes power switch 9 to be closed during this time. Electrical energy $e_5$ is therefore conducted to temperature radiator 2 from power supply 3. Measuring signal $e_3$ is present at an output c of measuring pickup 7. Measuring signal $e_3$ has a rapid rise-time and reaches its maximum amplitude in a short time.

The pulse width of pulse $e_2$ from pulse generator 10, pulse $e_2$ having a duration $t_1 - t_0$, is determined empirically or by calculation in response to the position in time of the peak value of measuring signal $e_3$. The duration is determined to ascertain that the maximum value of the measuring signal is reached with certainty during the time interval.

Upon the termination of pulse $e_2$, switch 9 is opened so as to interrupt the conduction of energy $e_5$ to temperature radiator 2. In this embodiment, switch 9 remains open for a period of time which is several times greater than the duration $t_1 - t_2$ of pulse $e_2$.

At a subsequent time $t_3$, clock generator 11 again delivers a signal $e_1$ which causes the process to be repeated with an overall period corresponding to the sum $(t_1 - t_0) + (t_3 - t_1)$, of the pulse and interval durations.

FIG. 2 is a schematic illustration of an automatic control circuit which may be used in the embodiment of FIG. 1. The automatic control circuit of FIG. 2 is connected to the circuit of FIG. 1 at terminals which are identified as a, b, c, and d. This circuit permits shorter "on" times to be achieved.

A bistable electronic power switch 9' is arranged between temperature radiator 2 and power supply 3. The closing of power switch 9' is achieved in response to an output pulse $e_1$ of clock generator 11. Clock output pulses $e_1$ have a spacing in time which corresponds to the sum of the pulse and interval durations.

Measurement signal $e_3$, which is present at terminal c of measurement pickup 7, is conducted to a maximum detector 12 which delivers a signal $e_4$ when the maximum value of measurement signal $e_3$ is reached. Signal $e_4$ corresponds in magnitude to measurement signal $e_3$ and is temporarily stored in a memory 13 until the next period so that a steady measurement signal is available for the succeeding processing of the measured value. In addition, output signal $e_4$ of maximum detector 12 also serves as a control signal which causes the opening of power switch 9'.

FIG. 4 is a timing diagram which shows the waveforms of signals $e_1$, $e_4$, $e_5$, and $e_3$ on parallel time scales. At time $t_0$ the control pulse $e_1$ of clock generator 11 closes switch 9', thereby completing the circuit between radiator 2 and power supply 3. This circuit conducts a flow of energy $e_5$ which causes radiation energy to be emitted by radiator 2, thereby producing a rise in measurement signal $e_3$ from measurement pickup 7. Switch 9' is opened at time $t_1$ in response to an output signal $e_4$ from maximum detector 12 which indicates that the maximum value of measurement signal $e_3$ has been reached. This interrupts flow $e_5$ until the beginning of the next period at time $t_3$.

In practice, almost the entire desired 100% modulation was achieved with nondispersive infrared gas analyzers operated in this manner. For pulse durations of 0.1 to 0.5 seconds, and intervals of 0.5 to 1.5 seconds. This arrangement permits all nondispersive infrared gas analyzers which operate with a modulated temperature radiator of signal-beam or dual-beam design with in-phase modulation of different receiver systems to be operated with considerably enhanced energy efficiency.

Although the invention has been disclosed in terms of specific embodiments and applications, other embodiments, in light of this teaching, can be configured by persons skilled in the pertinent art without departing from the spirit and scope of the invention. Accordingly, it is to be understood that the drawings and figures in this disclosure are proffered to facilitate comprehension of the invention and should not be construed to limit the scope thereof.

What is claimed is:

1. A nondispersive infrared gas analyzer of the type having a plurality of gas-filled chambers arranged in the propagation path of modulated infrared radiation, and a measuring pickup for producing an electrical measurement signal, the nondispersive infrared gas analyzer further comprising:
   pulsed energy supply means for producing electrical pulses having a duty cycle which is less than 1;
   infrared radiation means for producing infrared radiation which is modulated in response to said duty cycle of said pulsed energy supply means, said infrared radiation means having a predetermined continuous power rating; and
   pulse control means for terminating each of said electrical pulses from said pulsed energy supply means in response to a peak value of a corresponding pulse in the electrical measurement signal.

2. The nondispersive infrared gas analyzer of claim 1 wherein said duty cycle of said electrical pulses from said pulsed power supply means is within a range of between 0.1 to 0.5.

3. The nondispersive infrared gas analyzer of claim 1 wherein said infrared radiation means is operated to produce the modulated infrared radiation in pulses of infrared radiation having a maximum amplitude value which corresponds to several times said predetermined continuous power rating of said infrared radiation means.

4. The nondispersive infrared gas analyzer of claims 1, 2, or 3, wherein there are further provided:
   monostable power switch means having a first terminal for coupling to a source of electrical energy, a second terminal for coupling to said infrared radiation means, and a third terminal for receiving control signals;
   pulse generator means for producing said control signals at said third terminal of said monostable power switch means, said control signals having pulses of selectable duration; and
   clock generator means for producing periodic clock pulses having a period corresponding to the sum of said duration of one pulse in said control signals, and the duration of an interval between consecutive ones of said pulses.

5. The nondispersive infrared gas analyzer of claim 1 wherein there are further provided:
   bistable power switch means having a first terminal for coupling to a power supply, a second terminal for coupling to said infrared radiation source, and a third terminal for receiving control signals;
   clock generator means for producing said control signals to said third terminal of said bistable power switch means, said control signal being formed of periodic clock pulses having a period which corresponds to the sum of the duration of one of said clock pulses and the duration of an interval between consecutive ones of said clock pulses; and
   maximum value detector means responsive to the electrical measurement signal for producing an output signal which defines a time at which said bistable power switch means changes its conductive state.

* * * * *